(12) United States Patent
Kirkpatrick

(10) Patent No.: US 8,523,816 B2
(45) Date of Patent: Sep. 3, 2013

(54) AUTOMATIC RELEASE OF IV PUMP CASSETTE

(75) Inventor: Gregg Kirkpatrick, Fallbrook, CA (US)

(73) Assignee: CareFusion 303, Inc., San Diego, CA (US)

(*) Notice: Subject to any disclaimer, the term of this patent is extended or adjusted under 35 U.S.C. 154(b) by 39 days.

(21) Appl. No.: 12/869,590

(22) Filed: Aug. 26, 2010

(65) Prior Publication Data

US 2012/0053521 A1    Mar. 1, 2012

(51) Int. Cl.
*A61M 1/00* (2006.01)
(52) U.S. Cl.
USPC .......................................... 604/151
(58) Field of Classification Search
USPC ............ 604/80, 81, 151, 131; 335/289–294; 269/8
See application file for complete search history.

(56) References Cited

U.S. PATENT DOCUMENTS

| | | | | |
|---|---|---|---|---|
| 2,642,999 A * | 6/1953 | McPherson | ................... | 211/65 |
| 4,038,982 A * | 8/1977 | Burke et al. | ................... | 604/65 |
| 4,460,358 A * | 7/1984 | Somerville et al. | ........... | 604/250 |
| 5,006,050 A | 4/1991 | Cooke et al. | | |
| 5,302,093 A * | 4/1994 | Owens et al. | ................. | 417/474 |
| 6,608,539 B2 * | 8/2003 | Nobutoki et al. | ............... | 335/78 |
| 7,772,948 B2 * | 8/2010 | Grow et al. | ................... | 335/285 |
| 2010/0071192 A1 * | 3/2010 | Sarh et al. | ................... | 29/525.06 |
| 2012/0256715 A1 * | 10/2012 | Fullerton et al. | ............. | 335/285 |

FOREIGN PATENT DOCUMENTS

| | | |
|---|---|---|
| EP | 0296124 | 12/1988 |
| KR | 20020059588 | 7/2002 |

* cited by examiner

*Primary Examiner* — Laura Bouchelle
*Assistant Examiner* — Jenna Zhang
(74) *Attorney, Agent, or Firm* — McDermott Will & Emery LLP

(57) ABSTRACT

An intravenous (IV) pump is disclosed. The IV pump includes a housing, a permanent magnet, an electromagnet, and a switch configured to selectably energize or de-energize the electromagnet. The permanent magnet generates a magnetic field and the electromagnet, when energized, generates a magnetic field that approximately cancels the magnetic field of the permanent magnet.

21 Claims, 6 Drawing Sheets

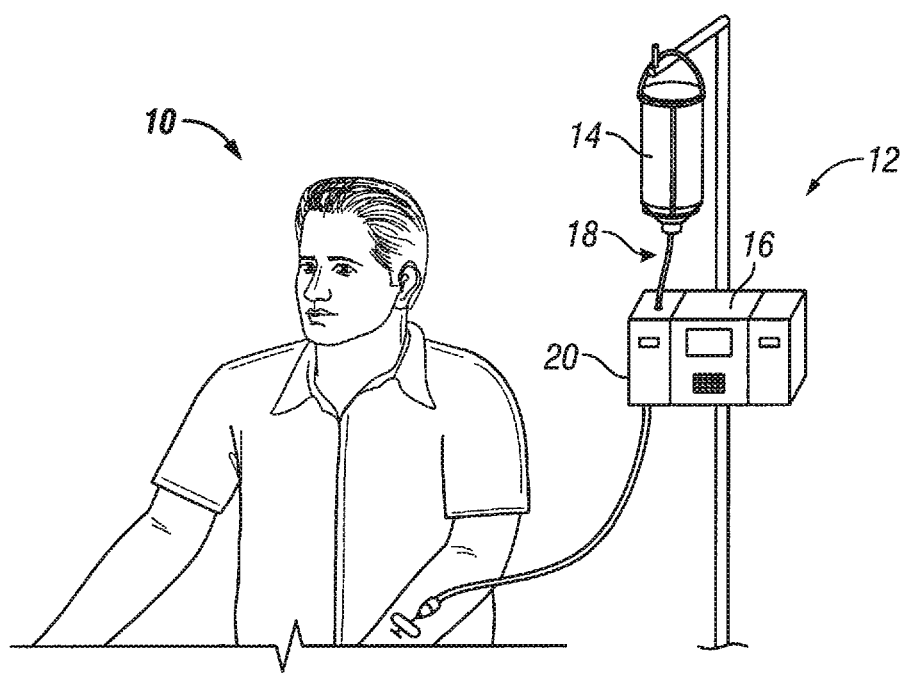
FIG. 1
*(Prior Art)*
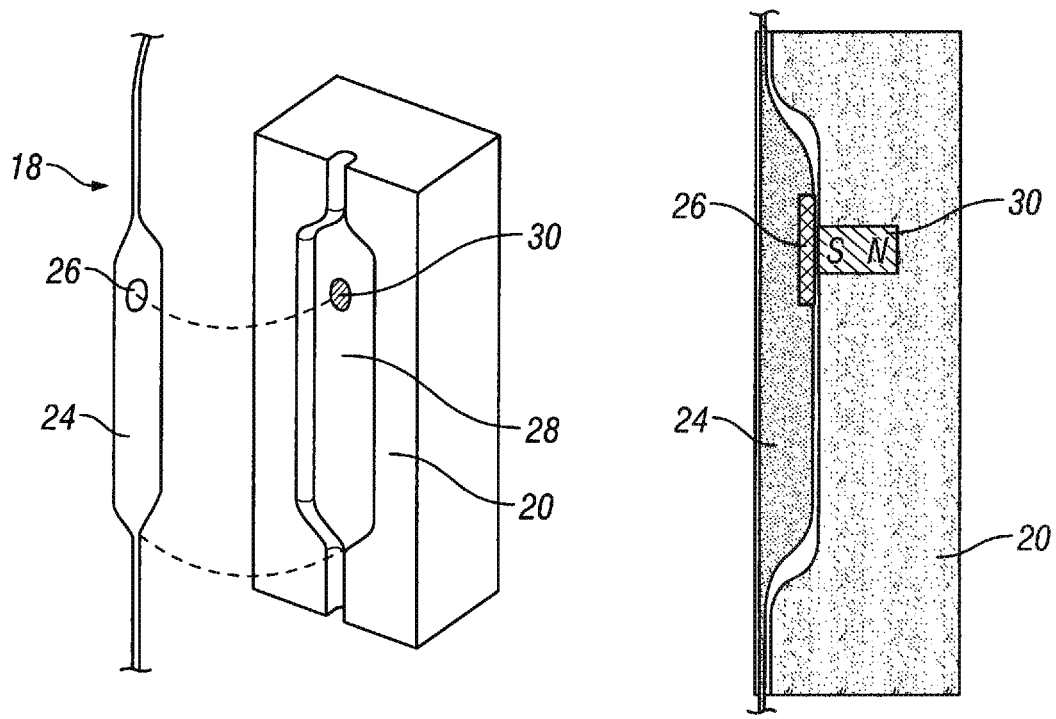
FIG. 2     FIG. 3

AUTOMATIC RELEASE OF IV PUMP CASSETTE

BACKGROUND

1. Field

The present disclosure generally relates to administration of medical fluid by infusion and, in particular, relates to a system and method of pumping infusion fluids.

2. Background

Infusion pumps have become commonplace within the healthcare world as a way to precisely administer intravenous (IV) fluids. Use of a pump in place of a simple roller clamp with an elevated fluid container to control the flow of the IV fluid allows more accurate and consistent control of the rate of delivery of the fluid to the patient.

Infusion sets designed for use with IV pumps may have a pumping chamber incorporated into the set, wherein the pumping chamber fits into a compartment in the IV pump. After completion of the infusion treatment, removal of the IV set and, in particular, the pumping chamber from the IV pump can be difficult. Some IV pumps use mechanical retention features to hold the pumping chamber in the proper position within the pump and provide an integrated lever that the nurse may use to pry the pumping chamber free from the pump. With such prying, however, there is an increased risk of damaging the IV set and consequently exposing the nurse and the patient to the content of the IV set.

SUMMARY

The IV set release system disclosed herein enables a user to remove an IV set from an IV pump without risk of damaging the IV set and potentially exposing the nurse or patient to the medication or other medical fluid. By reducing the retention force at the time of removal, this system provides improved retention during operation while also providing for safe and easy removal of the IV set at the conclusion of treatment.

An IV pump is disclosed that includes a housing, a permanent magnet attached to the housing, and an electromagnet attached to the housing. The permanent magnet generates a magnetic field and the electromagnet generates, when energized, a magnetic field that approximately cancels the magnetic field of the permanent magnet. The IV pump also includes a switch that is coupled to the electromagnet and configured to selectably energize or de-energize the electromagnet.

In another embodiment, an IV pump is disclosed that includes a housing and an attached electromagnet. The electromagnet generates, when energized, a magnetic field of either a first polarity or a second polarity, wherein the second polarity is opposite the first polarity. The IV pump also includes a switch that is coupled to the electromagnet and configured to energize the electromagnet to selectably generate a field of either the first polarity or the second polarity.

In another embodiment, an IV pump is disclosed that includes a housing, a first permanent magnet fixedly attached to the housing and a second permanent magnet movably attached to the housing, the second permanent magnet having a first position and a second position. The first permanent magnet generates a first magnetic field and the second permanent magnet generates a second magnetic field. The second magnetic field augments the first magnetic field when the second permanent magnet is in the first position and opposes the first magnetic field when the second permanent magnet is in the second position.

In another embodiment, an IV system is disclosed that includes an IV set with an attached ferromagnetic element, an IV pump that has a housing configured to accept a portion of the IV set, a permanent magnet attached to the housing, and an electromagnet attached to the housing. The permanent magnet attracts the ferromagnetic element of the IV set, and the electromagnet generates, when energized, a magnetic field that approximately cancels the magnetic field of the permanent magnet. The IV pump also includes a switch coupled between a power source and the electromagnet, the switch configured to energize and de-energize the electromagnet.

In another embodiment, an IV pump is disclosed that includes a housing, a magnetic attractive feature coupled to the housing wherein the magnetic attractive feature is configured to attract a pumping cassette comprising a magneto-sensitive material, and a magnetic cancellation feature coupled to the housing, wherein the magnetic cancellation feature is configured to controllably cancel the attraction of pumping cassette by the magnetic attractive feature.

A method of releasing an IV pump cassette from an IV pump is disclosed. The method includes the steps of substantially canceling a magnetic attractive force between a portion an IV pump and a portion of an IV set when the IV pump and IV set are in an attracted state, and removing the IV set from the IV pump when the magnetic attractive force is substantially cancelled.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 depicts a patient receiving medical fluid through an intravenous line using an IV pump.

FIG. 2 illustrates attachment of an infusion cassette to the IV pump of FIG. 1 according to certain embodiments of the present disclosure.

FIG. 3 is a cross-section of a portion of the IV pumping module of FIG. 2 showing an IV cassette 24 having a magneto-sensitive element and an IV pump having a permanent magnet according to certain embodiments of the present disclosure.

DETAILED DESCRIPTION

Figures 4A, 4B:
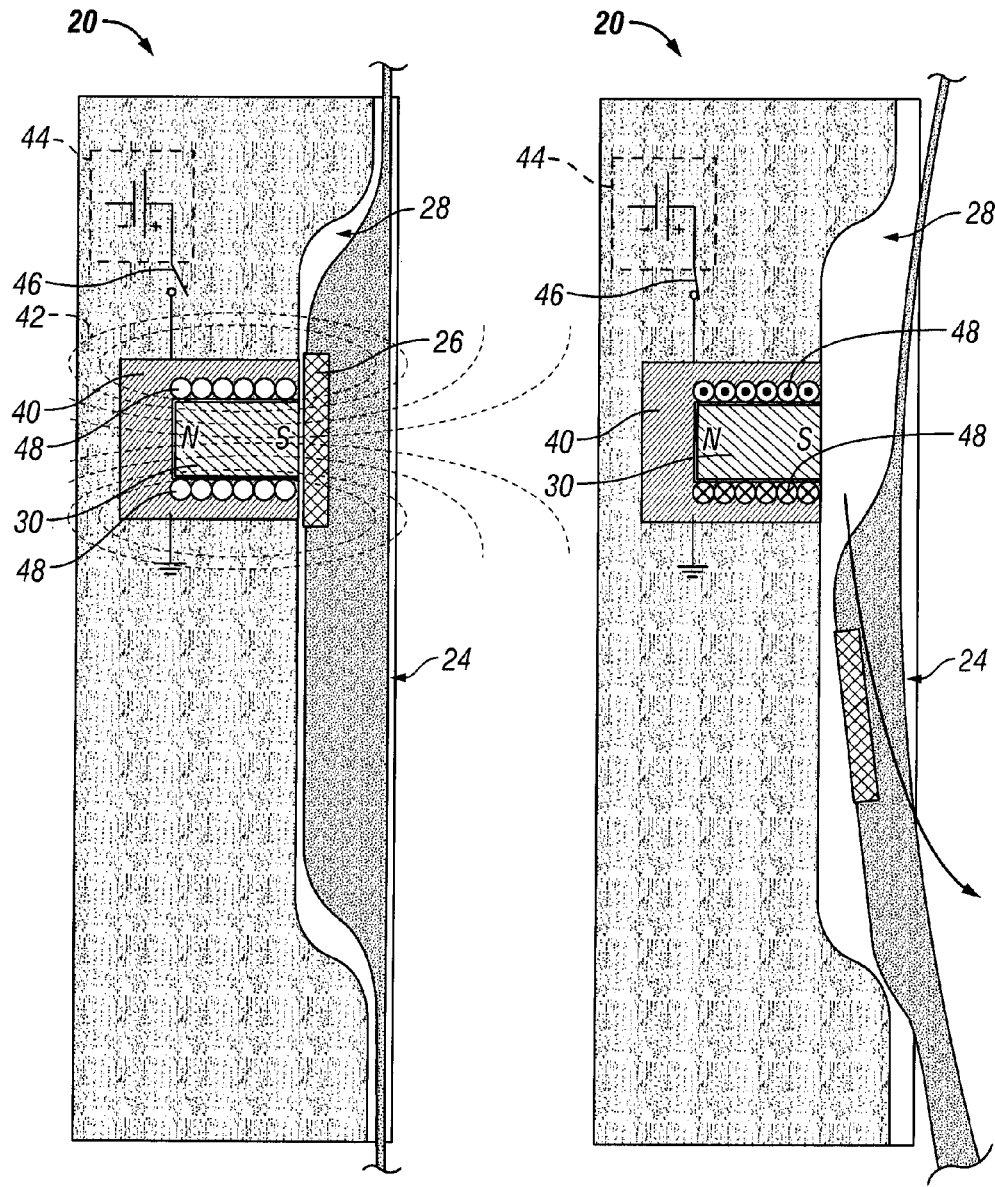
FIGS. 4A and 4B are cross-sections depicting an IV pumping module having a permanent magnet and an electromagnet according to certain embodiments of the present disclosure.

IV pumps are frequently configured to accept a portion of a disposable IV set and to provide a pumping action through manipulation of this portion of the IV set so that the permanent IV pump mechanisms are not exposed to the fluid being pumped. This avoids the risk of exposure of the healthcare provider to the medication or blood product that is being administered as well as reducing the risk of infection of the patient. After completion of treatment, the disposable IV set is removed from the IV pump and discarded. Since the pumping performance may be improved if the IV set is strongly held to the IV pump. Current designs may make it more difficult to remove the IV set from the IV pump without damaging the IV set.

Certain exemplary embodiments of the present disclosure include a system that comprises an IV set that incorporates a ferromagnetic element and an IV pump that is configured to first attract the ferromagnetic element to a defined position and retain the IV set during operation, and then to reduce the attractive force to release the IV set at the completion of treatment. In certain embodiments, a magnetic element replaces the ferromagnetic element and the IV pump includes an electromagnet that applies a force to the magnetic element to further assist in removing the IV set.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

FIG. 1 depicts a patient 10 receiving medical fluid through an IV set 18 using an IV pump 12. The fluid is provided, in this example, in a flexible bag 14 that is commonly hung above the IV pump 12 to provide a positive pressure at the pump 12. The IV pump 12 shown herein has a control unit 16 and an attached pumping module 20. The IV set 18 connects the fluid container 14 to the patient 10, and passes through the pumping module 20. The flow rate of the medical fluid is controlled by the pumping action of pumping module 20 under the control of control unit 16. In some configurations of IV pumps, the pumping module 20 is integrated with the control unit 16. The control unit 16 can also be located remotely from the pumping module 20 in certain embodiments. Hereinafter, the use of the phrase "pumping module" refers to the pumping portion of any IV pump, whether integrated or separate.

FIG. 2 illustrates attachment of an infusion cassette 24 to the IV pump 20 of FIG. 1 according to certain embodiments of the present disclosure. The term "cassette" is used herein to refer to a portion of an IV set 18 that is configured to be attached or positioned within a portion of the IV pump 20 during use. This cassette 24 may comprise rigid elements or may be completely made of flexible materials, or a combination of rigid and flexible materials. The cassette 24 comprises a magneto-sensitive element 26 comprising a magneto-sensitive material, i.e. a material that is attracted by a magnetic field. This magneto-sensitive material may or may not be permanently magnetized. This magneto-sensitive material is incorporated into the structure of magneto-sensitive element 26 in this embodiment. In other embodiments, the magneto-sensitive material is applied as a coating to the surface of magneto-sensitive element 26. The pumping module 20 has a recess 28 that is configured to accept and retain cassette 24 such that pumping elements (not shown) of pumping module 20 can manipulate cassette 24 to pump fluid. Pumping module 20 further comprises a magnetic actuator 30 configured to attract the attractive element 20 of cassette 24 and provide at least a portion of the retention force to retain cassette 24 within the recess 28. Although only a single magneto-sensitive element 26 and magnetic actuator 30 are depicted in FIG. 2, certain embodiments of the present disclosure have a plurality of such pairs.

FIG. 3 is a cross-section of a portion of the IV pumping module 20 of FIG. 2 showing an IV cassette 24 having a magneto-sensitive element 26 and an IV pump 20 having a permanent magnet 30 according to certain embodiments of the present disclosure. It can be seen that the permanent magnet 30 is configured to attract and retain the magneto-sensitive element 26, thereby attaching and retaining the cassette 24 to the pumping module 20. This same retention feature, however, increases the effort required to remove the pumping cassette 24 from pumping module 20 after treatment is complete. It is desirable to reduce this retention force when it is time to remove pumping module 24.

FIGS. 4A and 4B are cross-sections showing an exemplary embodiment of an IV pumping module 20 having a permanent magnet 30 and an electromagnet 40 according to certain embodiments of the present disclosure. Like the pumping module 20 of FIG. 3, the pumping module 20 of FIG. 4A has a permanent magnet 30 that attracts and retains the magneto-sensitive element 26 of the cassette 24. In addition, the pumping module 20 of FIG. 4A includes an arrangement that helps to release the cassette 24 from pump module 20. This release aids the nurse in removing the cassette 24 with less risk of rupturing the cassette 24 and exposing the medical fluids to the nurse and patient.

The release arrangement includes an electromagnet 40 that, in the depicted embodiment of FIG. 4A, is wrapped around the permanent magnet 30 such that the magnetic fields created by electromagnet 40 and permanent magnet 30 are approximately coincident. Electromagnet 40 is powered by a power source 44, represented herein as a battery. In certain embodiments, power source 44 is an external source of electrical power. A switch 46 is coupled between power source 44 and electromagnet 40 such that switch 46 controls the flow of current through the windings 48 of electromagnet 40.

FIG. 4A depicts the cassette 24 magnetically attached to the pumping module 20 and, thus, in position to be acted upon by the pumping module 20 to pump fluid. Permanent magnet 30 is located with one of its north-south poles flush with the surface of recess 28 at a position that corresponds to the location of a magneto-sensitive element 26 of cassette 24 when the cassette 24 is properly located in recess 28. In this example, the windings 48 of electromagnet 40 are shown in cross-section as circles with dots in the center for wire sections having current flowing toward the viewer and with crosses in the center for wire sections having current flowing away from the viewer. In FIG. 4A, switch 46 is open and the power source 44 is not connected to the electromagnet 40 and, therefore, no current is flowing through the windings 48. The permanent magnet 30 generates a magnetic field 42, shown as a series of broken lines representing the magnetic field lines. Magneto-sensitive element 26 of cassette 24 has been attracted by magnetic field 42 such that cassette 24 is attached and retained in the recess 28 of the pumping module 20.

FIG. 4B depicts a configuration of the IV pump 20, for example, following completion of a pumping operation. Switch 46 is closed and power source 44 is connected to the electromagnet 40 and, therefore, current is flowing through the windings 48. The direction that current flows will govern the polarity of the field that is generated. Depending on the orientation of the permanent magnet 30, shown with the north pole on the left in FIG. 4A, the current is controlled to flow in a specified direction through the windings 48 in order to generate a magnetic field that opposes the magnetic field generated by permanent magnet 30, with the strength of the two fields being approximately equal. When the two fields are of opposite polarity and equal strength, as shown in the configuration of FIG. 4B, there is no net magnetic field and therefore no attractive force applied to magneto-sensitive element 26. As the magnetic field 42 provides the only retention force, in this example, the cancellation of the magnetic field 42 by the electromagnet 40 allows the cassette 24 to slip out of the recess 28 by gravity, for example, as depicted by the arrow in FIG. 4B. Alternately, a nurse can easily remove the cassette 24 by hand without danger of rupturing the cassette 24.

Figure 5A:
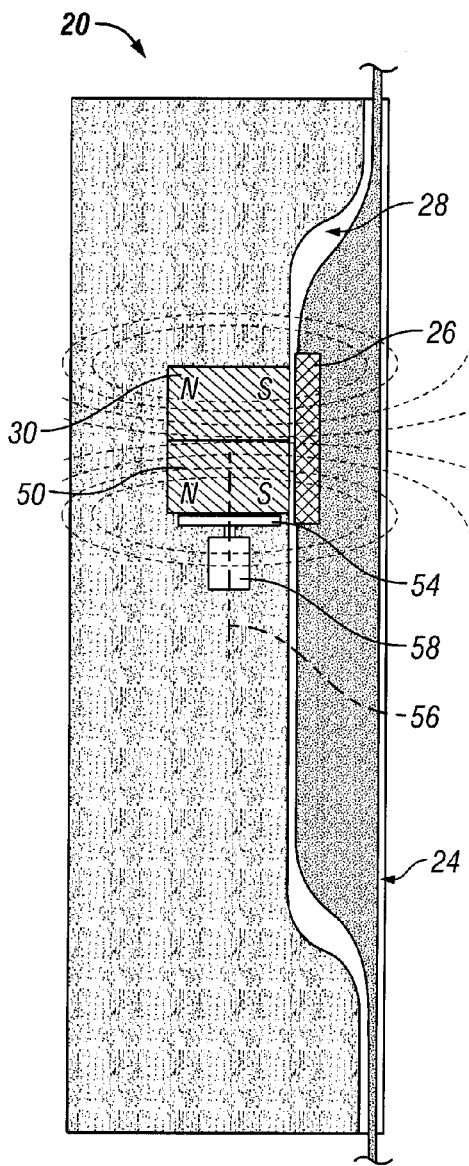
FIGS. 5A and 5B are cross-sections showing an IV pump having two permanent magnets according to certain embodiments of the present disclosure.
Figure 5B:
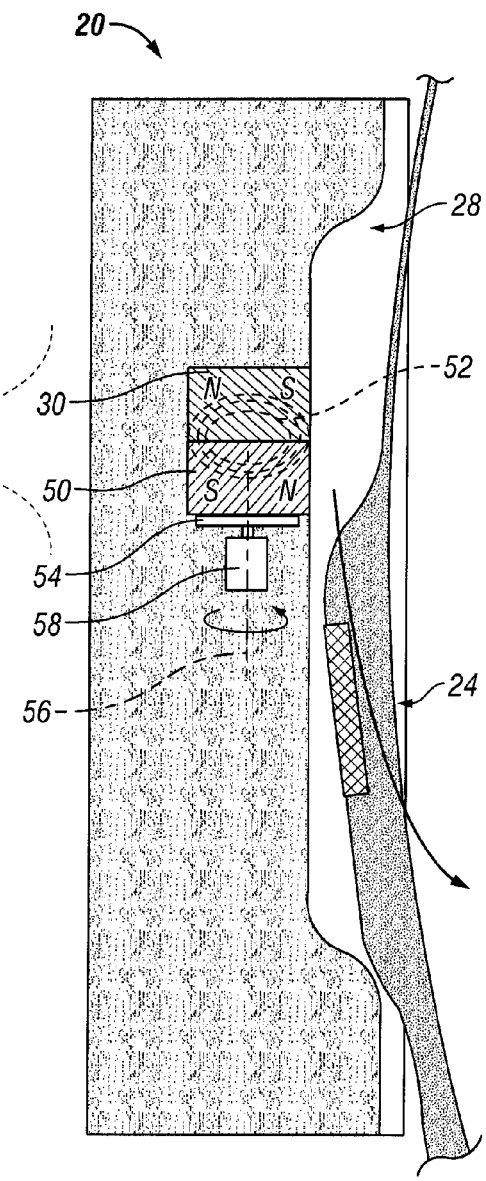

FIGS. 5A and 5B are cross-sections showing an exemplary embodiment of an IV pump 20 having a permanent magnet 30 and a permanent magnet 50 according to certain embodiments of the present disclosure. Permanent magnet 50 is coupled to a turntable 54 that can rotate at least 180 degrees about axis 56. Turntable 54 is coupled to a rotary actuator 58 that has a first position such that the north pole of permanent magnet 50 is aligned with the north pole of permanent magnet 30 and a second position such that the north pole of permanent magnet 50 is aligned with the south pole of permanent magnet 30. The rotary actuator 58 is controlled to move between the first and second positions. Other arrangements for rotatably mounting a magnet, such as embedding the magnet in a disk, and moving the magnet from one position to a second position, such as with a solenoid or motor, will be known to those of ordinary skill in the art.

In the position shown in FIG. 5A, rotary actuator 58 is in the first position and, consequently, the poles of permanent magnet 50 are aligned with those of permanent magnet 30, producing a combined magnetic field 52. As with the configuration of FIG. 4A, magnetic field 52 attracts magneto-sensitive element 26 and attaches and retains cassette 24 in recess 28 of pumping module 20 so that cassette 24 can be used in a pumping operation.

In FIG. 5B, rotary actuator 58 has moved to the second position and, consequently, the north pole of permanent magnet 50 is adjacent to the south pole of permanent magnet 30. In this configuration, the magnetic fields of permanent magnets 30 and 50 are tightly coupled as shown with the magnetic field 52 being totally within permanent magnets 30 and 50 and, as a result, there is no external field. In the absence of a net external magnetic field, there is no attraction force applied to magneto-sensitive element 26 and cassette 24 slips out of the recess 28, as depicted by the arrow in FIG. 5B.

Figures 6, 7:
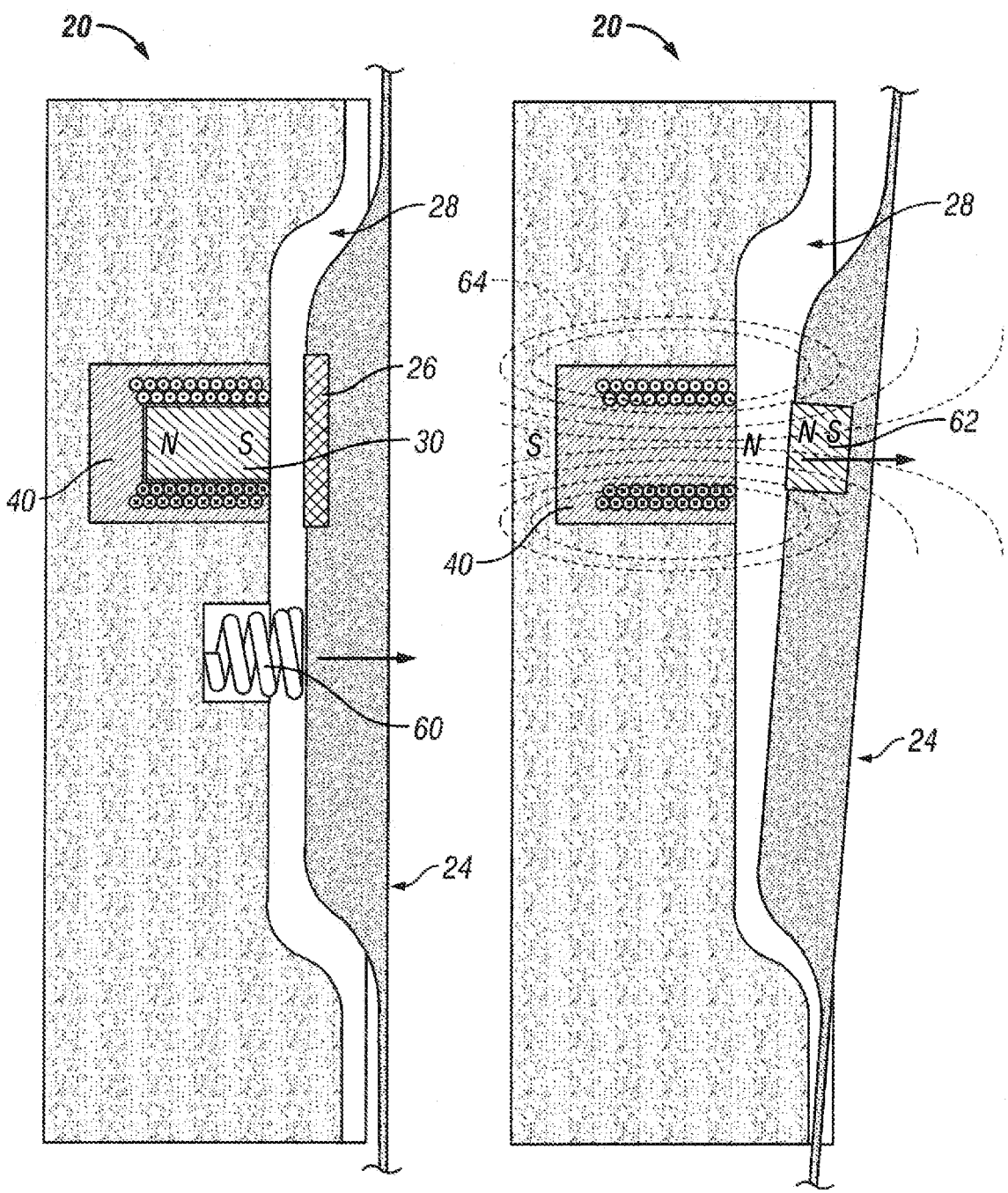
FIG. 6 is a cross-section showing an IV pump having a spring element to assist in removing a cassette according to certain embodiments of the present disclosure.
FIG. 7 is a cross-section showing another embodiment of an IV pump configured to assist in removing a cassette according to certain embodiments of the present disclosure.

FIG. 6 is a cross-section showing an embodiment of an IV pump 20 having a biasing element 60 to assist in removing the cassette 24 according to certain embodiments of the present disclosure. In the embodiment of FIG. 6, the biasing element is a helical spring, although other types of biasing element can also be used, such as elastically compressible foam or a flexible cantilever. In this example, the pumping module 20 comprises a permanent magnet 30 and an electromagnet 40 that are configured as in FIG. 4A to attract and retain the magneto-sensitive element 26 of the cassette 24. Biasing element 60 is in compression when the cassette 24 is fully seated in the recess 28, with a compressive force that is small compared to the force applied by the permanent magnet 30. When the electromagnet 40 is energized, the magnetic field of the permanent magnet 30 is approximately cancelled, and the compressive force of the biasing element 60 is larger than the residual force of the two opposing magnetic fields. Thus, the force applied by biasing element 60, indicated by the arrow, is sufficient to force the cassette 24 out of the recess 28, further assisting in the removal of cassette 24 from the pumping module 20.

FIG. 7 is a cross-section showing an embodiment wherein the cassette 24 has a magnetic element 62 and the electromagnet 40 of the pumping module 20 can apply force to the magnetic element 62 to assist in removing the cassette 24 according to certain embodiments of the present disclosure. Cassette 24 is retained in pumping module 20 by the magnetic field generated by electromagnet 40, when the polarity of the magnetic field is such that the poles are in the same direction as those of the magnetic element 62, i.e. the south pole of the magnetic field of the electromagnet field 64 is adjacent to the north pole of the magnetic element 62. However, in the situation illustrated in FIG. 7, the direction of the current flowing through the windings of electromagnet 50 is such as to create a magnetic field 64 that repulses magnetic element 62, i.e. the north poles of the two fields are adjacent, as shown in FIG. 7. This creates a force, indicated by the arrow, pushing cassette 24 out of recess 28, assisting in the removal of cassette 24 from the pumping module 20. Hence, the current can be made to flow in the electromagnet 40 to cause attraction and retention of the cassette 24, and also in a direction to cause repulsion and ejection of the cassette 24.

Figure 8A:
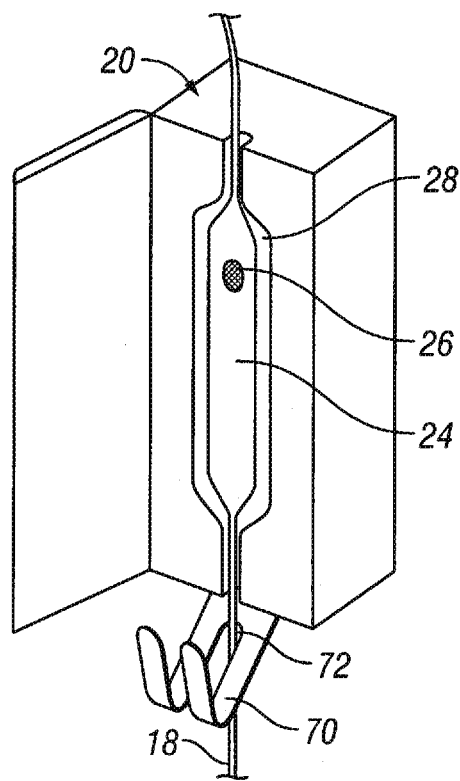
FIGS. 8A-8B are perspective views of a pumping module having a receiver to catch a cassette during removal according to certain embodiments of the present disclosure.
Figure 8B:
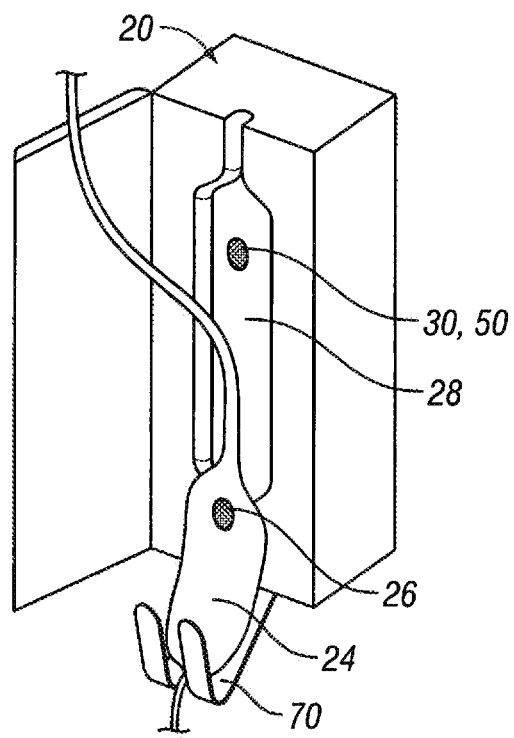

FIGS. 8A-8B are perspective views of an embodiment of a pumping module 20 having a sloped receiver 70 under the recess 28 to catch the cassette 20 when removing the cassette 20 according to certain embodiments of the present disclosure. FIG. 8A depicts the pumping module 20 of FIG. 4A with the electromagnet 50 (not visible) de-energized such that an attractive force is applied by the permanent magnet 30 to magneto-sensitive element 26 and the cassette 24 is retained in recess 28. A sloped receiver is attached to the pumping module 20 at the bottom, having a slot 72 configured such that the tubing of IV set 18 passes through the slot while the IV pump 12 is in operation. In FIG. 8B, the electromagnet 50 has been energized, cancelling the magnetic field of permanent magnet 30, and therefore cancelling the attractive force applied to magneto-sensitive element 26. Cassette 24 is therefore released and slides out of recess 28, whereupon cassette 24 is caught by sloping receiver 70. In this example, slot 72 captures the tubing of IV set 18 and guides the cassette 24 into the sloping receiver 70. This enables the nurse to press the switch 46, or other control element of IV pump 12, that energizes electromagnet 50 with one hand without requiring her to have her other hand ready to catch the released cassette 24. This simplifies the workflow as well as avoids the risk of the cassette 24 becoming damaged or contaminated by falling on the floor.

Figure 9:
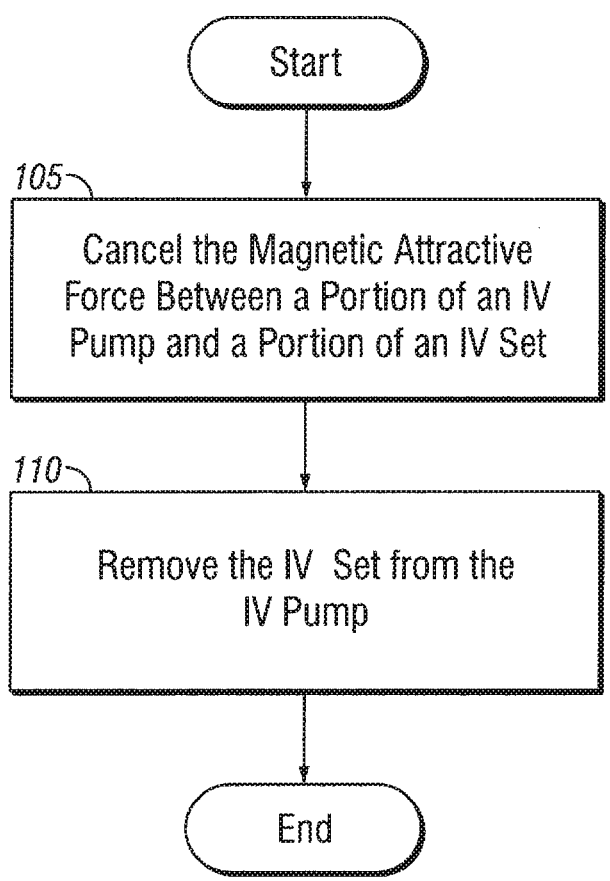
FIG. 9 is a flowchart depicting the process of releasing a cassette from an IV pumping module according to certain embodiments of the present disclosure.

FIG. 9 is a flowchart depicting the process of releasing a cassette 24 from an IV pumping module 20 according to certain embodiments of the present disclosure. In step 105, the magnetic attractive force between a portion of an IV set 18 and a portion of an IV pump 12 is cancelled by one or more of the arrangements disclosed herein. In step 110, the IV set 18 is removed from the IV pump 12. The portion of the IV set 12 is, in this example, the cassette 24 described in at least FIG. 4A herein.

It can be seen that the disclosed embodiments of the retention and release mechanisms provide a secure and releasable attachment of a cassette of an IV set to a pumping module of an IV pump. By actively cancelling the magnetic field and therefore reducing the retention force, the amount of effort required to remove the cassette is decreased, reducing the risk of damage to the cassette and the risk of injury to the nurse and patient. This releasable attachment may be accomplished through a plurality of combinations of permanent magnets and electromagnets.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

The term "magneto-sensitive" is used herein to refer to a material that is attracted by a magnetic field and may or may not be magnetized. Example of magneto-sensitive materials include ferromagnetic materials such as iron, some steels, nickel, and cobalt and ferrites such as barium ferrite $BaO:6Fe_2O_3$. Iron, for example, may be magnetized or unmagnetized. Unmagnetized iron is attracted by a magnetic field but does not generate its own magnetic field. Pairs of materials will be attracted to each other if the first material is magnetized and the second material is a magneto-sensitive material, which implies that the second material may be magnetized as well. Two non-magnetized magneto-sensitive materials will not be attracted to each other.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An intravenous (IV) pump, comprising:
 a housing configured to accept a cassette that forms a portion of an IV set; and
 a mechanism for coupling the cassette to the housing, the mechanism comprising:
  a permanent magnet coupled to the housing, the permanent magnet generating a magnetic field;
  an electromagnet coupled to the housing, the electromagnet configured to generate, when energized, a magnetic field that approximately cancels the magnetic field of the permanent magnet; and
  a switch coupled to the electromagnet, the switch configured to selectably energize or de-energize the electromagnet.

2. The IV pump of claim 1, wherein:
 the cassette comprises an attached magneto-sensitive element; and
 the permanent magnet is configured to attract the magneto-sensitive element and thereby attach and retain the cassette to the housing when the electromagnet is not energized.

3. The IV pump of claim 2, further comprising a spring element that is attached to the housing, the spring element configured to apply a force to the cassette to eject the cassette from the housing, the force of the spring element being sufficient to overcome a residual attractive force between the IV pump and the cassette that is present when the electromagnet is energized.

4. An intravenous (IV) pump, comprising:
 a housing configured to accept a cassette that forms a portion of an IV set having an attached magnetic element;
 an electromagnet attached to the housing, the electromagnet configured to, when energized, generate a magnetic field of either a first polarity or a second polarity, wherein the second polarity is opposite the first polarity; and
 a switch attached to the housing and coupled to the electromagnet, the switch configured to energize the electromagnet to selectably generate a field of either the first polarity or the second polarity,
 wherein the electromagnet is configured to, when energized in the first polarity, attract the magnetic element and thereby attach and retain the IV set to the housing.

5. The IV pump of claim 4, wherein the electromagnet is further configured to, when energized in the second polarity, repulse the magnetic element and thereby assist in removing the IV set from the IV pump.

6. The IV pump of claim 4, wherein the portion of the IV set that is accepted by the housing is a pumping cassette and the magnetic element is attached to the pumping cassette.

7. An intravenous (IV) pump, comprising:
 a housing configured to accept a cassette that forms a portion of an IV set having an attached magneto-sensitive element;

a first permanent magnet fixedly attached to the housing, the first permanent magnet generating a first magnetic field; and a second permanent magnet movably attached to the housing, the second permanent magnet having a first position and a second position and generating a second magnetic field;

wherein the second magnetic field augments the first magnetic field when the second permanent magnet is in the first position; and wherein the second magnetic field opposes the first magnetic field when the second permanent magnet is in the second position.

8. The IV pump of claim 7, wherein the first permanent magnet is configured to attract the magneto-sensitive element and thereby attach and retain the IV set to the housing when the second permanent magnet is in the first position.

9. The IV pump of claim 8, wherein the second magnetic field approximately cancels the first magnetic field when the second permanent magnet is in the second position.

10. The IV pump of claim 9, further comprising a spring element that is attached to the housing, the spring element configured to apply a force to the IV set to eject the IV set from the housing, the force of the spring element being sufficient to overcome a residual attractive force between the IV pump and the IV set that is present when the first magnetic field is opposed by the second magnetic field.

11. The IV pump of claim 8, wherein the portion of the IV set that is accepted by the housing is a pumping cassette and the magneto-sensitive element is attached to the pumping cassette.

12. An intravenous (IV) system, comprising:
an IV set comprising a cassette having an attached magneto-sensitive element; and
an IV pump comprising:
a housing configured to accept the cassette; and
a mechanism for coupling the cassette to the housing, the mechanism comprising:
a permanent magnet attached to the housing, the permanent magnet configured to attract the magneto-sensitive element of the cassette;
an electromagnet attached to the housing, the electromagnet configured to generate a magnetic field when energized such that the magnetic field generated by the electromagnetic approximately cancels the magnetic field of the permanent magnet; and
a switch coupled between a power source and the electromagnet, the switch configured to energize and de-energize the electromagnet.

13. The IV system of claim 12, further comprising a bias element that is attached to the housing, the bias element configured to apply a force to the IV set to eject the IV set from the housing, the force of the bias element sufficient to overcome a residual attractive force between the IV pump and the IV set that is present when the electromagnet is energized.

14. An intravenous (IV) pump, comprising:
a housing configured to accept a cassette that forms a portion of an IV set, the cassette comprising a magneto-sensitive material; and
a mechanism for coupling the cassette to the housing, the mechanism comprising:
a magnetic attractive feature coupled to the housing, the magnetic attractive feature configured to create a first magnetic field so as to attract the magneto-sensitive material;
a magnetic cancellation feature coupled to the housing, the magnetic cancellation feature configured to create a second magnetic field that is at least substantially equal in magnitude and opposite in direction to the first magnetic field in a region surrounding the magneto-sensitive material so as to substantially cancel the attraction of the cassette by the magnetic attractive feature; and
a control element operatively coupled to the magnetic cancellation feature, the control element configured to cause the magnetic cancellation feature to create the second magnetic field.

15. The IV pump of claim 14, wherein:
the magneto-sensitive material of the cassette comprises a magnetic material;
the magnetic cancellation feature is configured to create a second magnetic field that is larger in magnitude and opposite in direction to the first magnetic field such that the combination of the first and second magnetic fields applies a net repulsive force to the cassette.

16. The IV pump of claim 14, further comprising a biasing element, configured to repulse the pumping cassette, wherein the magnitude of the repulsion of the biasing element is less than the magnitude of the attraction of the magnetic attractive feature and greater than the net attraction of the combined action of the magnetic attractive feature and the magnetic cancellation feature.

17. The IV pump of claim 14, wherein the magnetic cancellation feature comprises an electromagnet.

18. The IV pump of claim 14, wherein:
the magnetic attractive feature comprises an electromagnet; and
the magnetic cancellation feature comprises the control element is configured to reduce the current flowing through the electromagnet, thereby cancelling the attraction of cassette.

19. The IV pump of claim 14, wherein:
the pumping cassette comprises a magnetic material; and
the magnetic cancellation feature comprises an electromagnet that creates a second magnetic field that repulses the pumping cassette.

20. The IV pump of claim 14, wherein:
the magnetic attractive feature comprises a first permanent magnet coupled to the housing;
the magnetic cancellation feature comprises a second permanent magnet coupled to the housing;
one or both of the first and second permanent magnets are movable relative to the other permanent magnet such that their magnetic poles can be aligned in a common direction or in opposite directions;
the pumping cassette is attracted when the poles of the first and second permanent magnets are aligned with their poles in a common direction; and
the attraction of the pumping cassette is cancelled when the poles of the first and second permanent magnets are aligned with their poles in opposite directions.

21. A method of releasing an intravenous (IV) set from an IV pump, the method comprising the steps of:
coupling a cassette that forms a part of the IV set to a housing of the IV pump that is configured to accept the cassette using a magnetic attractive element that is coupled to the housing and configured to create a first magnetic field so as to attract a magneto-sensitive material that is part of the cassette;
actuating a control element that is operable coupled to a magnetic cancellation feature that is coupled to the housing and configured to create a second magnetic field that is at least substantially equal in magnitude and opposite in direction to the first magnetic field in a region surrounding the magneto-sensitive material so as to substantially cancel the attraction of the cassette by the magnetic attractive feature;

removing the cassette of the IV set from the housing of the IV pump when the first magnetic field is substantially cancelled.

\* \* \* \* \*